DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED SEPTEMBER 3, 1974

926 O.G. 12

T926,014

ROUTINE FOR IDENTIFYING A P-WAVE TRAIN

Raymond E. Bonner, Yorktown Heights, N.Y., assignor to International Business Machines Corporation, Armonk, N.Y.

Continuation of abandoned application Ser. No. 212,154, Dec. 27, 1971. This application Feb. 28, 1974, Ser. No. 446,848

Int. Cl. G06f *15/42*

U.S. Cl. 444—1

1 Sheet Drawing. 20 Pages Specification

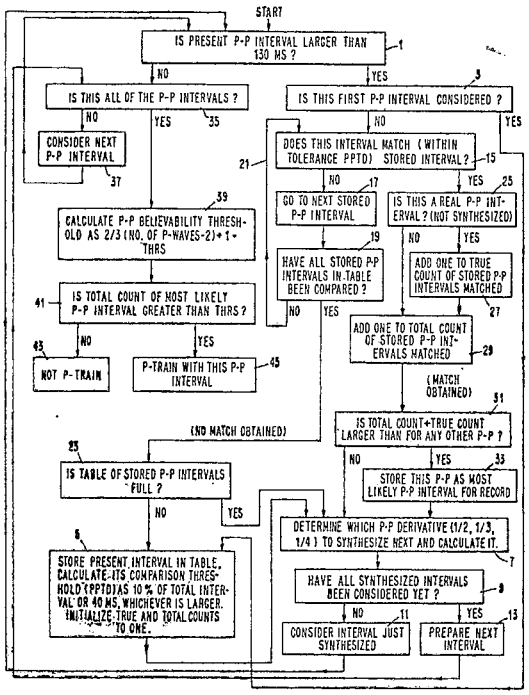

The figure shows a programming routine for automatically processing an electrocardiograph signal in a digital computer to determine whether a regularly spaced train of P-waves is present in the previously found P-like bumps or waves of the signal. The respective P-to-P time intervals between successive P-like waves of the signal are sequentially compared to each of the different P-to-P time intervals previously stored in a table of P-to-P time intervals. Each time a P-to-P time interval fails to match, within a predetermined degree of tolerance, intervals previously stored in the table, it is added to the table as a new interval. Each time an interval is added to the table, synthesized fractional subintervals thereof are likewise compared and added, if they fail to match. A separate count is maintained of the number of times each interval in the table is matched. The count of the interval which is matched most often is compared with a believability threshold to determine whether a regularly spaced train of P-waves is present.

ROUTINE FOR IDENTIFYING A P-WAVE TRAIN
Original Filed Dec. 27, 1971
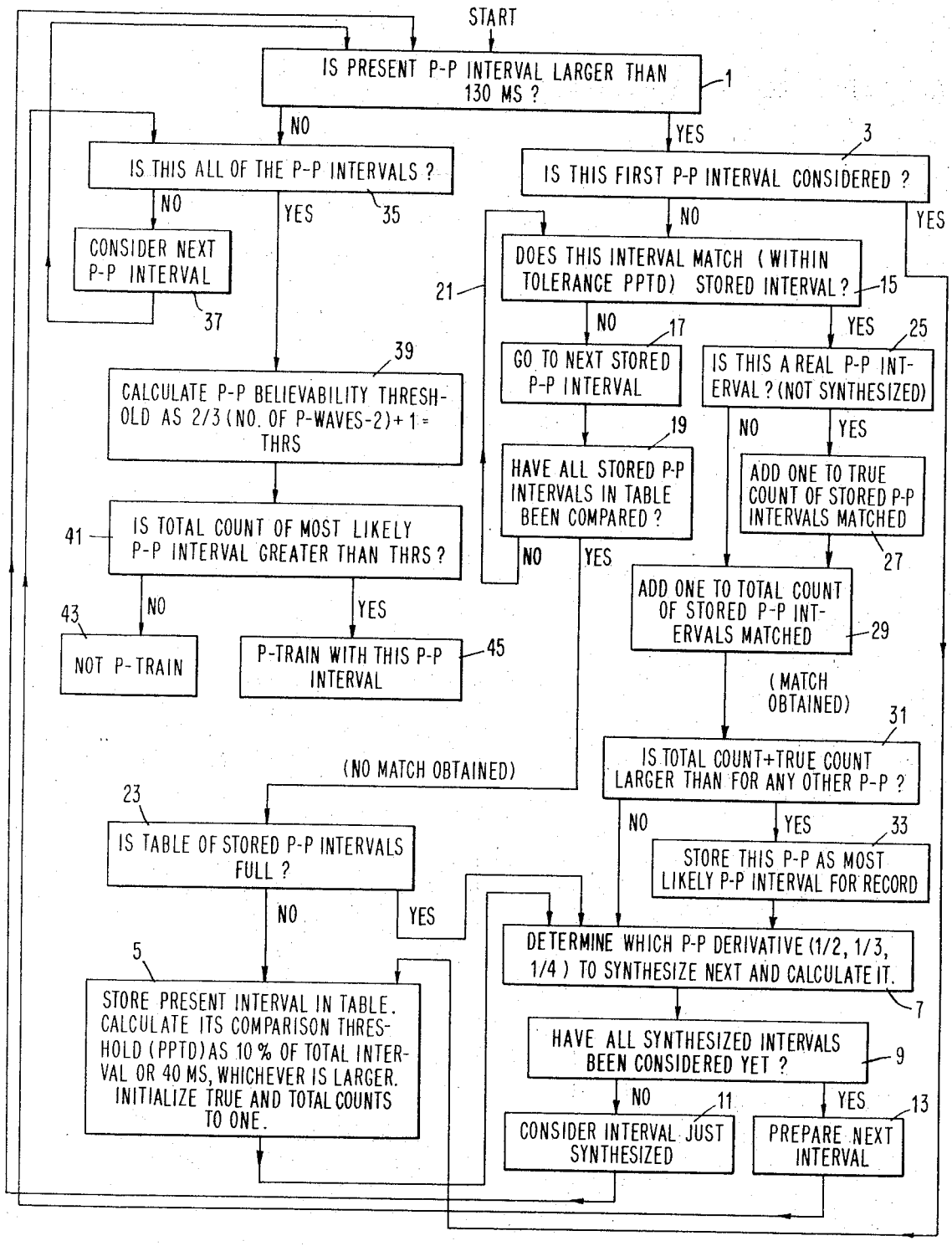
INVENTOR
RAYMOND E. BONNER
BY John A. Jordan
ATTORNEY